United States Patent [19]

Matsuyama et al.

[11] Patent Number: 5,512,465
[45] Date of Patent: Apr. 30, 1996

[54] PROCESS FOR PRODUCING OPTICALLY ACTIVE 1,3-BUTANEDIOL

[75] Inventors: Akinobu Matsuyama; Yoshinori Kobayashi, both of Niigata, Japan

[73] Assignee: Daicel Chemical Industries, Ltd., Osaka, Japan

[21] Appl. No.: 247,849

[22] Filed: May 23, 1994

Related U.S. Application Data

[62] Division of Ser. No. 778,918, Dec. 31, 1991, Pat. No. 5,336,619.

[30] Foreign Application Priority Data

Oct. 15, 1990 [JP] Japan ...................... 2-276100

[51] Int. Cl.$^6$ ........................................ C12P 7/18
[52] U.S. Cl. ................ 435/158; 435/280; 435/822; 435/911
[58] Field of Search ................ 435/280, 158, 435/822, 911

[56] References Cited

FOREIGN PATENT DOCUMENTS

| | | |
|---|---|---|
| 0556387 | 8/1993 | European Pat. Off. . |
| 58-204187 | 11/1983 | Japan . |
| 61-191631 | 8/1986 | Japan . |
| 1320997 | 12/1989 | Japan . |
| 231684 | 1/1990 | Japan . |
| 024185 | 2/1990 | Japan . |
| 2195897 | 2/1990 | Japan . |
| 264533 | 10/1990 | Japan . |
| 3228686 | 10/1991 | Japan . |
| 8910410 | 1/1989 | WIPO . |

OTHER PUBLICATIONS

ATCC Catalogue of Bacteria, Phages and DNA vectors, pp. 38, 150 (1985).
ATCC Catalogue of Fungi/Yeasts, pp. 104, 350 (1987).
IFO List of Cultures pp. 16, 20, 26, 45–50, 52 (1988).
JCM Catalogue of Strains pp. 63, 118, 119, 121 (1992).
DSM Catalogue of Strain pp. 99, 100 (1989).
C. Neuberg et al. (1918) *Biochem. Z.*, 92:96–110.
Murakami et al., (1980) Bull Chemical Society of Japan 53(5):1356–60.
Levene et al. (1931) J. Biol. Chem. 94:361–366.

*Primary Examiner*—Michael G. Wityshyn
*Assistant Examiner*—S. Saucier
*Attorney, Agent, or Firm*—Birch, Stewart, Kolasch & Birch

[57] ABSTRACT

Optically active 1,3-butanediol can be obtained by treating an enantiomorphic mixture of 1,3-butanediol with a microorganism or cells thereof which have been ground, acetone-treated, or lyophilized capable of acting on an enantiomorphic mixture of 1,3-butanediol so as to leave (R)- or (S)-1,3-butanediol as such. Further, optically active 1,3-butanediol can be obtained by treating 4-hydroxy-2-butanone with a microorganism or cells thereof which have been ground, acetone-treated, or lyophilized capable of asymmetrically reducing the 4-hydroxy-2-butanone into (R)- or (S)-1,3-butanediol.

13 Claims, No Drawings

PROCESS FOR PRODUCING OPTICALLY ACTIVE 1,3-BUTANEDIOL

This application is a divisional of U.S. application Ser No. 07/778,918, filed on Dec. 31, 1991, now U.S. Pat. No. 5,336,619, the entire contents of which are hereby incorporated by reference.

FIELD OF THE INVENTION

The present invention relates to a process for producing optically active 1,3-butanediol. More particularly, it relates to a process for producing optically active 1,3-butanediol which comprises treating an enantiomorphic mixture of 1,3-butanediol with a specific microorganism or cells thereof which have been ground, acetone-treated, or lyophilized, and recovering the remaining optically active 1,3-butanediol.

Optically active 1,3-butanediols are important materials for synthesizing various drugs such as antibiotics.

They are further usable as starting materials for synthesizing azetidinone derivatives, which are intermediate materials for tenem and carbapenem antibiotics, as well as various drugs and agricultural chemicals.

DESCRIPTION OF RELATED ART

Known examples of processes for producing optically active 1,3-butanediol include (1) one comprising resolving a racemic mixture of 1,3-butanediol synthesized chemically by using an agent for optical resolution (Japanese Patent Laid-Open No. 191631/1986); and (2) another one comprising asymmetric synthesis from 4-hydroxy-2-butanone by using Raney nickel catalyst which has been treated with an optically active compound [Japanese Patent Laid-Open No. 204187/1983 and Bull. Chem. Soc. Jpn., 53, 1356–1360(1980)]. However, it is disadvantageous that each of these processes (1) and (2) requires the use of an expensive agent for optical resolution or an expensive catalyst, and that, further, process (2) gives only poor optical purity. Accordingly, it has been urgently required to establish a process for economically and conveniently producing optically active 1,3-butanediol having high optical purity.

In addition, there have been reported some processes for producing optically active 1,3-butanediol by using a microorganism [refer to, for example, WO 89/10410, corresponding to EP Application 89-905185, and U.S. Ser. No. 449929; Levene and A. Walti, J. Biol. Chem., 94(1931) P.A. 361–366; and Carl Neuberg and Elisabeth Kub, Biochem. Z., 92 (1918), 96–110].

Japanese Patent Laid-Open No. 31684/1991 describes a process for producing optically active 1,3-butanediol via asymmetrical reduction using a certain microorganism.

DISCLOSURE OF THE INVENTION

The present inventors have given their attention to a process for economically and conveniently producing optically active 1,3-butanediol of high optical purity by rising a microorganism, and attempted to search for microorganisms suitable for this purpose. As a result, they have discovered that microorganisms selected from among those belonging to the genera Clavispora, Kloeckera and Schizoblastosporion act on an enantiomorphic mixture of 1,3-butanediol so as to leave (R)-1,3-butanediol as such, while microorganism selected from among those belonging to the genera Eremascus, Syringospora, Sporopachydermia, Zygoascus and Zygozyma acts on an enantiomorphic mixture of 1,3-butanediol so as to leave (S)-1,3-butanediol as such, thus completing the present invention.

The microorganisms usable in the present invention include those belonging to the genera Clavispora, Kloeckera and Schizoblastosporion and capable of acting on an enantiomorphic mixture 1,3-butanediol so as to leave (R)-1,3-butanediol as such and those belonging to the genera Eremascus, Syringospora, Sporopachydermia, Zygoascus and Zygozyma capable of acting on an enantiomorphic mixture of 1,3-butanediol so as to leave (S)-1,3-butanediol as such.

Particular examples of the microorganism capable of acting on an enantiomorphic mixture of 1,3-butanediol so as to leave (R)-1,3-butanediol as such include *Clavispora lusitaniae* IFO 1019, *Kloeckera africana* IFO 0869 and *Schizoblastosporion kobayashii* IFO 1644.

On the other hand, particular examples of the microorganism capable of acting on an enantiomorphic mixture of 1,3-butanediol so as to leave (S)-1,3-butanediol as such include *Eremascus fertilis* IFO 0691, *Syringospora claussenii* IFO 0759, *Sporopachydermia lactativora* IFO 1867, *Zygoascus hellenicus* IFO 1575 and *Zygozyma oligophaga* IFO 10360.

These microorganisms may be suitably used in the present invention regardless of form (i.e., wild strains, mutants or recombinants obtained through genetic engineering techniques such as cell fusion or gene recombination).

Microorganisms to which IFO Nos. are assigned are described in *List of Cultures*, 8th ed., Vol. 1(1988) published by institute for Fermentation, Osaka (IFO) and available therefrom.

Any medium may be used for incubating the microorganism to be used in the present invention, so long as the microorganism can grow therein. Thus any carbon source available to the microorganism (for example, sugars such as glucose, fructose, sucrose and dextrin, alcohols such as sorbitol, ethanol and glycerol, organic acids such as fumaric acid, citric acid; acetic acid and propionic acid and salts thereof, hydrocarbons such as paraffin and mixtures thereof) may be used. As a nitrogen source, for example, ammonium salts of inorganic acids such as ammonium chloride, ammonium sulfate and ammonium phosphate, ammonium salts of organic acids such as ammonium fumarate and ammonium titrate, inorganic or organic nitrogenous materials such as meat extract, yeast extract, corn steep liquor, casein hydrolysate and urea and mixtures thereof may be used. The medium may further contain nutritional sources commonly employed for culturing microorganisms, for example, inorganic salts, trace metal salts and vitamins. Furthermore, factors for promoting the growth of the microorganism, those for elevating the productivity of the target compound, and materials effective in maintaining the pH value of the medium at a desired level may be added thereto, if required.

The microorganism may be incubated at a medium pH value of from 3.0 to 9.5(preferably from 4 to 8) at an incubation temperature of from 20° to 45° C. (preferably from 25 to 37° C. ) under such conditions (aerobic or anaerobic) as to suit the growth of the microorganism for from 5 to 120 hours (preferably from 12 to 72 hours).

A means for preparing optically active 1,3-butanediol from the enantiomorphic mixture of 1,3-butanediol includes a method of using the culture medium as such and adding the enantiomorphic mixture of 1,3-butanediol thereto, and a method whereby the cells are separated by, for example, centrifugation, optionally washed and then suspended in a buffer solution or water, and the enantiomorphic mixture of 1,3-butanediol is added to the resulting suspension and is reacted. It is sometimes advantageous to add a carbon source, for example, glucose or sucrose, to the reaction mixture as an energy source. The cells may be used either in the form of viable cells or in a treated state (for example, as ground, acetone-treated or lyophilized cells). These cells or treated cells may be used as in the immobilized form obtained by a known method (for example, the polyacrylamide gel method, sulfur-containing polysaccharide gel methods such as the carageenan gel method, alginic acid gel method or agar gel method). Furthermore, enzymes obtained from the treated cells by combining known purifying techniques may be used therefor.

The enantiomorphic mixture of 1,3-butanediol may be used either as such or dissolved in water or an inert organic solvent or dispersed in, for example, a surfactant. The entire enantiomorphic mixture may be added at once at the initiation of the reaction, or alternately, it may be added in portions.

The reaction may be effected within a pH range of from 3 to 10(preferably from 5 to 9) at a temperature of from 10° to 60° C. (preferably from 20° to 40° C.) for 1 to 120 hours under stirring or by standing Optically active 1,3-butanediol of a higher optical purity can be obtained by prolonging the reaction period, though the amount of the remaining 1,3-butanediol is decreased thereby. The concentration of the substrate may preferably range from 0.1 to 10%, though the present invention is not restricted thereby.

The remaining optically active 1,3-butanediol may be easily recovered by a common purifying technique (for example, extraction with an organic solvent, distillation or column chromatography) either directly from the reaction mixture or after separating the cells.

The present inventors have given their attention to a process for economically and conveniently producing optically active 1,3-butanediol of high optical purity by using a microorganism and attempted to search for microorganisms suitable for this purpose. As a result, they have discovered that a microorganism selected from among those belonging to the genera Rhodococcus, Gordona and Streptomyces acts on an enantiomorphic mixture of 1,3-butanediol so as to leave (R)-1,3-butanediol as such while a microorganism selected from among those belonging to the genera Rhodococcus and Gordona acts on an enantiomorphic mixture of 1.3-butanediol so as to leave (S)-1,3-butanediol as such, thus completing the present invention.

The microorganisms usable in the present invention include those belonging to the genera Rhodococcus, Gordona and Streptomyces and capable of acting on an enantiomorphic mixture of 1,3-butanediol so as to leave (R)-1, 3-butanediol as such and those belonging to the genera Rhodococcus and Gordona capable of acting on an enantiomorphic mixture of 1,3-butanediol so as to leave (S)-1, 3-butanediol as such.

Particular examples of the microorganism capable of acting on an enantiomorphic mixture of 1,3-butanediol so as to leave (R)-1,3-butanediol as such include *Rhodococcus erythropolis* DSM 43200, *Rhodococcus erythropolis* JCM 2893, *Rhodococcus rubropertinctus* DSM 43346, *Rhodococcus rhodochrous* JCM 2157, *Rhodococcus equi* JCM 1311, *Gordona bronchialis* JCM 3198 and *Streptomyces netropsis* HUT 6068. On the other hand, particular examples of the microorganism capable of acting on an enantiomorphic mixture of 1,3-butanediol so as to leave (S)-1,3-butanediol as such include *Rhodococcus rhodochrous* DSM 43273, *Rhodococcus erythropolis* DSM *Rhodococcus roseus* JCM 2158 and *Gordona sputi* JCM 3228.

These microorganisms may be suitably used in the present invention regardless of form (i.e., wild strains, mutants or recombinants obtained through genetic engineering techniques such as cell fusion or gene recombination).

Microorganisms to which JCM Nos. are assigned are described in Catalog of Strains, 4th ed. (1989) published by Japan Collection of Microorganisms, RIKEN and available therefrom. Those to which DSM Nos. are assigned are described in Catalog of Strains (1989) published by Deutsche Sammlung yon Mikroorganismen (DSM) and available therefrom. Those to which HUT Nos. are assigned are available from Department of Fermentation Engineering, Faculty of Technology, Hiroshima University.

The present inventors further conducted intensive studies in order to develop a process for producing optically active 1,3-butanediol through asymmetric reduction. As a result, they have newly discovered that a microorganism selected from among those belonging to the genera Agrobacterium, Azotobacter, Bordetella, Brettanomyces, Dekkera, Endomyces, Eremascus, Erwinia, Fusarium, Geotrichum, Gibberella, Glomerella, Gonatobotryum, Klebsiella, Micrococcus, Mycobacterium, Neosartorya, Oospora, Pachysolen, Paecilomyces, Paracoccus, Preussia, Saccharomyces, Saccharomycopsis, Serratia, Syringospora, Septoria, Sporopachydermia, Talaromyces, Westerdykella, Zygoascus and Zygozyma produces (R)-1,3-butanediol by asymmetrically reducing 4-hydroxy-2-butanone while a microorganism selected from among those belonging to the genera Aciculoconidium, Brettanomyces, Clavispora, Cochliobolus, Corynespora, Dactylium, Echinopodospora, Enterobacter, Hamigera, Heiminthosporium, Kloeckera, Nectria, Pseudomonas, Phialocephala, Rhodotorula, Saccharomyces, Sterigmatomyces and Schizoblastosporion produces (S)-1, 3-butanediol by asymmetrically reducing 4-hydroxy-2-butanone, thus completing the present invention.

The microorganisms usable in the present invention include those belonging to the genera Agrobacterium, Azotobacter, Bordetella, Brettanomyces, Dekkera, Endomyces, Eremascus, Erwinia, Fusarium, Geotrichum, Gibberella, Glomerella, Gonatobotryum, Klebsiella, Micrococcus, Mycobacterium, Neosartorya, Oospora, Pachysolen, Paecilomyces, Paracoccus, Preussia, Saccharomyces, Saccharomycopsis, Serratia, Syringospora, Septoria, Sporopachydermia, Talaromyces, Westerdykella, Zygoascus and Zygozyma and capable of producing (R)-1,3-butanediol by asymmetrically reducing 4-hydroxy-2-butanone and those belonging to the genera Aciculoconidium. Brettanomyces, Clavispora, Cochliobolus, Corynespora, Dactylium, Echinopodospora, Enterobacter, Hamigera, Helminthosporium, Kloeckera, Nectria, Pseudomonas, Phialocephala, Rhodotorula, Saccharomyces, Sterigmatomyces and Schizoblastosporion and capable of producing (S)-1,3-butanediol by asymmetrically reducing 4-hydroxy-2-butanone.

Particular examples of the microorganism capable of producing (R)-1,3-butanediol from 4-hydroxy-2-butanone include *Agrobacterium radiobacter* IFO 12664, *Azotobacter chroococcum* IFO 12994. *Bordetella bronchiseptica* IFO 13691, *Brettanomyces abstines* DSM 70726, *Dekkera bruxellensis* IFO 1590, *Endomyces decipiens* IFO 0102, *Eremascus fertilis* IFO 0691, *Erwinia carotovora* subsp. *carotovora* IFO 3830, *Fusarium oxysporum* IFO 7152, *Fusarium selani* IFO 5232, *Geotrichum fragrans* JCM 1749, *Gibberella fujikuroi* IFO 5268, *Glomerella cingulata* IAM 8050, *Gonatobotryum apiculatum* IFO 9098, *Klebsiella pneumo-* nias IFO 12059, *Micrococcus luteus* IFO 3333, *Micrococcus roseus* IFO 3764, *Mycobacterium smegmatis* IFO 3153, *Neosartorya fischeri* var. *spinosa* IFO 5955, *Oospora astringenes* IFO 7001, *Pachysolen tannophilus* IFO 1007, *Paecilomyces variotii* IFO 4855, *Paracoccus denitrificans* IFO 12442, *Preussia terricola* IFO 7893, *Saccharomyces cerevisiae* IAM 0216, *Saccharomycopsis fibuligera* IFO 0103, *Serratia marcescens* IAM 1105, *Syringospora claussenii* IFO 0759, *Septoria glycines* IFO 5294, *Sporopachydermia lactativora* IFO 1867, *Talaromyces flavus* var. *flavus* IFO 7231, *Westerdykella multispora* IFO 5813, *Zygoascus hellenicus* IFO 1575 and *Zygozyma oligophaga* IFO 10360.

On the other hand, particular examples of the microorganism capable of producing (S)-1,3-butanediol from 4-hydroxy-2-butanone include *Aciculoconidium aculeatum* IFO 10124, *Brettanomyces anomalus* IFO 0796, *Clavispora lusitaniae* IFO 1019, *Cochliobolus miyabeanus* IFO 6631, *Corynespora cassiicola* IFO 6724, *Dactylium dentroides* ATCC 46032, *Echinopodospora jamaicensis* IFO 9819, *Enterobacter cloacae* ATCC 7256, *Hamigera avellanea* IFO 7721, *Helminthosporium sigmoideum* var. *irregulare* IFO 5273, *Kloeckera africana* IFO 0869, *Nectria cinnabarina* IFO 6821, *Pseudomonas diminuts* IFO 12697, *Phialocephala bacterospora* IFO 8770, *Rhodotorula glutinis* IFO 0395, *Saccharomyces cerevisiae* AHU 3402, *Sterigmatomyces elviae* DSM 70852 and *Schizoblastosporion kobayashii* IFO 1644.

These microorganisms may be suitably used in the present invention regardless of form (1.e., wild strains, mutants or recombinants obtained through genetic engineering techniques such as cell fusion or gene recombination).

Microorganisms to which IFO Nos. are assigned are described in List of Cultures, 8th ed., Vol. 1(1988) published by Institute for Fermentation, Osaka (IFO) and available therefrom. Those to which AHU Nos. are assigned are described in Catalogue of Cultures, 4th ed. (1987) published by Japanese Federation of Culture Collections of Microorganisms (JFCC) and available from Faculty of Agriculture, Hokkaido University. Those to which JCM Nos. are assigned are described in Catalog of Strains, 3rd ed. (1986) published by Japan Collection of Microorganisms, RIKEN and available therefrom. Those to which ATCC Nos. are assigned are described in Catalogue of Bacteria Phages rDNA Vectors, 16th ed. (1985) and Catalogue of Fungi/Yeast, 17th Ed. (1987) published by American Type Culture Collection (ATCC) and available therefrom. Those to which DSM Nos. are assigned are described in Catalog of strains (1983) published by Deutsch Sammlung von Mikroorganismen (DSM) and available therefrom. Those to which IAM Nos. are assigned are available from Institute of Applied Microbiology, the University of Tokyo.

In the present invention, a means for the reduction reaction includes a method of using the culture medium as such, and a method whereby the cells are separated by, for example, centrifugation, optionally washed and resuspended in a buffer or water, and then 4-hydroxy-2-butanone is added to the obtained suspension and is reacted. It is sometimes preferable to add a carbon source such as glucose and sucrose as an energy source during this reaction. The viable cells may be used as such. Alternately, treated cells (for example, ground, acetone-treated or lyophilized cells) may be used. These cells or treated cells may be immobilized by a known method, for example, the polyacrylamide gel method, sulfur-containing polysaccharide gel methods such as carageenan gel method, alginic acid gel method or agar gel method. Furthermore, enzymes purified from the treated cells by combining some known procedures may be used therefor.

The 4-hydroxy-2-butanone may be used as such. Alternately, it may be dissolved in water or an inert organic solvent or dispersed in a surfactant. It may be added either at once at the initiation of the reaction, or in portions.

In the present invention, the reduction reaction may be effected at a pH value of from 3 to 9 (preferably from 5 to 8), at a temperature of from 10° to 60° C. (preferably from 20° to 40° C. ) for 1 to 120 hours either under stirring or standing. The concentration of the substrate may preferably range from 0.1 to 10%, though the present invention is not restricted thereby.

The optically active 1,3-butanediol thus formed may be easily collected by a common purification procedure (for example, extraction with an organic solvent, distillation, or column chromatography) either directly from the reaction mixture or after separating the cells.

EXAMPLES

To further illustrate the present invention, and not by way of limitation, the following Examples will be given.

In each Example, 1,3-butanediol in the reaction mixture could be easily determined by gas chromatography column: Thermon 3000, 2m, temperature: 130° C. ), while the optical purity was measured by acetylating the obtained optically active 1,3-butanediol with the use of acetyl chloride by a conventional method and then high-performance liquid chromatography by using an optical resolution column (column: Chiralcel OB produced by Diacel Chemical Industries, Ltd., solvent: n-hexane/2-propanol (19 : 1), wavelength: 220 nm, flow rate: 0.5 ml/min.) (retention time of (S)-form: 15 minutes, that of (R)-form: 19.3 minutes).

EXAMPLE 1

| Medium for preparing cells: | |
| --- | --- |
| glucose | 1.0% |
| yeast extract | 0.3% |
| peptone | 0.5% |
| 1,3-butanediol | 0.5% |
| $K_2HPO_4$ | 0.1% |
| $MgSO_4 \cdot 7H_2O$ | 0.05% |
| | pH7.2. |

100 ml of the above-mentioned medium for preparing cells was introduced into a 500-ml Sakaguchi flask and sterilized. Then the medium was inoculated with each microorganism listed in Table 1. After incubating under shaking at 30° C. for 48 hours, the cells were separated by centrifugation and washed once with physiological saline. In this way viable cells were obtained.

Next, 50-ml of distilled water were introduced into a 500 ml Sakaguchi flask and the above-mentioned viable cells were suspended therein. 0.5 g of 1,3-butanediol in a racemic mixture was added thereto and the mixture was incubated under reciprocal shaking at 30° C. for 48 hours.

After the completion of the reaction, the cells were removed by centrifugation. Then the obtained supernatant was saturated with sodium chloride and extracted with 50-ml of ethyl acetate. The ethyl acetate layer was analyzed by gas chromatography and thus the remaining 1,3-butanediol was determined.

Next, the ethyl acetate was dehydrated over anhydrous sodium sulfate. After solvent removal, the obtained syrup was acetylated with acetyl chloride by a conventional method, dissolved in a solvent, and analyzed by high performance liquid chromatography to determine the absolute configuration and optical purity of the 1,3-butanediol thus obtained.

Table 1 summarizes the results.

TABLE 1

| Microorganism | Remaining 1,3-butanediol (mg/ml) | Absolute configuration | Optical purity of 1,3-butanediol (% e.e.) |
|---|---|---|---|
| Clavispora lusitaniae IFO 1019 | 3.7 | R | 43 |
| Kloeckera africana IFO 0869 | 8.7 | R | 48 |
| Schizoblastosporion kobayasii IFO 1644 | 4.5 | R | 87 |
| Eremascus fertilis IFO 0691 | 3.6 | S | 90 |
| Syringospora claussenii IFO 0759 | 0.2 | S | 61 |
| Sporopachydermia lactativora | 0.1 | S | 95 |
| Zygoascus hellenicus IFO 1575 | 4.1 | S | 98 |
| Zygozyma oligophaga IFO 10360 | 0.2 | S | 99 |

Table 2 summarizes the results.

TABLE 2

| Microorganism | Absolute configuration | Optical purity (% e.e.) | Remaining 1,3-butanediol (mg/ml) |
|---|---|---|---|
| Rhodococcus erythropolis DSM 43200 | R | 90 | 4.3 |
| Rhodococcus erythropolis JCM 2893 | R | 80 | 4.5 |
| Rhodococcus rubropertinctus DSM 43346 | R | 89 | 5.1 |
| Rhodococcus rhodochrous JCM 2157 | R | 71 | 4.0 |
| Rhodococcus equi JCM 1311 | R | 71 | 3.8 |
| Gordona bronchialis JCM 3198 | R | 77 | 3.3 |
| Streptomyces netropsis HUT 6068 | R | 51 | 6.5 |
| Rhodococcus rhodochrous DSM 43273 | S | 60 | 6.3 |
| Rhodococcus erythropolis DSM 43274 | S | 58 | 6.4 |
| Rhodococcus roseus JCM 2158 | S | 53 | 6.3 |
| Gordona sputi JCM 3228 | S | 56 | 6.0 |

EXAMPLE 2

| Medium for preparing cells: | |
|---|---|
| bonito meat extract | 1.0% |
| polypeptone | 1.0% |
| sodium chloride | 0.5% |
| | pH7.3. |

100 ml of the above-mentioned medium for preparing cells was introduced into a 500-ml Sakaguchi flask and sterilized. Then the medium was inoculated with each microorganism listed in Table 2. After incubating under shaking at 30° C. for 48 hours, the cells were separated by centrifugation and washed once with physiological saline. Thus In this way viable cells were obtained.

Next, 50-ml of distilled water were introduced into a 500-ml Sakaguchi flask and the above-mentioned viable cells were suspended therein. 0.5 g of 1,3-butanediol in a racemic mixture was added thereto and the mixture was incubated under reciprocal shaking at 30° C. for 48 hours.

After the completion of the reaction, the cells were removed by centrifugation. Then the obtained supernatant was saturated with sodium chloride and extracted with 50 ml of ethyl acetate. The ethyl acetate layer was analyzed by gas chromatography and thus the remaining 1,3-butanediol was determined.

Next, the ethyl acetate was dehydrated over anhydrous sodium sulfate. After solvent removal, the obtained syrup was acetylated with acetyl chloride by a conventional method, dissolved in a solvent and analyzed by high performance liquid chromatography to determine the absolute configuration and optical purity of the 1,3-butanediol thus obtained.

EXAMPLE 3

A YM medium comprising 0.3% yeast extract, 0.3% malt extract, 0.5% peptone and 2% of glucose (pH: 6.0) was used for strains of yeast-like fungi, while a YPM medium comprising 2% glucose, 0.5% yeast extract, 0.3% peptone, 0.3% meat extract, 0.2% $(NH_4)_2HPO_4$ and 0.1% $KH_2PO_4$(pH1,7) was used for strains of bacteria. 100 ml of each medium were introduced into a 500-ml Sakaguchi flask and sterilized. Then the medium was inoculated with each microorganism listed in Table 3. After incubating under reciprocal shaking at 27° C. for 48 hours, the cells were separated by centrifugation and washed once with physiological saline. In this way viable cells were obtained.

Next, 50-ml of distilled were introduced into a 500 ml Sakaguchi flask and the above-mentioned viable cells were suspended therein. 5 g of glucose were added to the obtained suspension followed by reciprocal shaking at 27° C. for 10 minutes. Then 0.5 g of 4-hydroxy-2-butanone was added thereto and the mixture was incubated under reciprocal shaking at 27° C. for 20 hours.

After the completion of the reaction, the cells were removed by centrifugation. Then the obtained supernatant was saturated with sodium chloride and extracted with 50 ml of ethyl acetate. The ethyl acetate layer was analyzed by gas chromatography to examine the reaction yield.

Next, the ethyl acetate layer was dehydrated over anhydrous sodium sulfate. After solvent removal, the obtained syrup was acetylated with acetyl chloride by a conventional method, dissolved in a solvent and analyzed by high performance liquid chromatography to determine the absolute configuration and optical purity of the product. Table 3 summarizes the results.

TABLE 3

| Microoganism | Reaction yield (%) | Absolute configuration | Optical purity (% e.e.) |
|---|---|---|---|
| Agrobacterium radiobacter IFO 12664 | 27 | R | 41 |
| Azotobacter chroococcum IFO 12994 | 44 | R | 53 |
| Bordetella bronchiseptica IFO 13691 | 33 | R | 40 |
| Brettanomyces abstines DSM 70726 | 42 | R | 66 |
| Dekkera bruxellensis IFO 1590 | 51 | R | 54 |
| Endomyces decipiens IFO 0102 | 38 | R | 40 |
| Eremascus fertilis IFO 0691 | 34 | R | 38 |
| Erwinia carotovora subsp. carotovora IFO 3830 | 25 | R | 51 |
| Fusarium oxysporum IFO 7152 | 85 | R | 95 |
| Fusarium selani IFO 5232 | 91 | R | 96 |
| Geotrichum fragrans JCM 1749 | 62 | R | 60 |
| Gibberella fujikuroi IFO 5268 | 55 | R | 42 |
| Glomerella cingulata IAM 8050 | 47 | R | 90 |
| Gonatobotryum apiculatum IFO 9098 | 39 | R | 44 |
| Klebsiella pneumoniae IFO 12059 | 49 | R | 35 |
| Micrococcus luteus IFO 3333 | 47 | R | 37 |
| Micrococcus roseus IFO 3764 | 51 | R | 41 |
| Mycobacterium smegmatis IFO 3153 | 50 | R | 40 |
| Neosartorya fischeri var. spinosa IFO 5955 | 39 | R | 88 |
| Oospra astringenes IFO 7001 | 41 | R | 53 |
| Pachysolen tannophilus IFO 1007 | 47 | R | 61 |
| Paecilomyces variotii IFO 4855 | 53 | R | 55 |
| Paracoccus denitrificans IFO 12442 | 56 | R | 37 |
| Preussia terricola IFO 7893 | 42 | R | 42 |
| Saccharomyces cerevisiae IAM 0216 | 45 | R | 47 |
| Saccharomycopsis fibuligari IFO 0103 | 58 | R | 60 |
| Serratia marcescens IAM 1105 | 32 | R | 37 |
| Syringospora claussenii IFO 0759 | 41 | R | 58 |
| Septoria glycines IFO 5294 | 53 | R | 54 |
| Sporopachydermia lactativora IFO 1867 | 78 | R | 95 |
| Talaromyces flavus var. flavus IFO 7231 | 48 | R | 47 |
| Westerdykella multispora IFO 5813 | 48 | R | 42 |
| Zygoascus hellenicus IFO 1575 | 81 | R | 97 |
| Zygozyma oligophaga IFO 10360 | 88 | R | 95 |
| Aciculoconidium aculeatum IFO 10124 | 45 | S | 56 |
| Brettanomyces anonalus IFO 0796 | 44 | S | 61 |
| Clavispora lusitaniae IFO 1019 | 51 | S | 48 |
| Cochliobolus miyabeanus | 45 | S | 55 |
| IFO 6631 | | | |
| Corynespora cassiicola IFO 6724 | 58 | S | 61 |
| Dactylium dentroides ATCC 46032 | 43 | S | 65 |
| Echinopodospora jamaicensis IFO 9819 | 40 | S | 70 |
| Enterobacter cloacae ATCC 7256 | 40 | S | 51 |
| Hamigera avellanea IFO 7721 | 43 | S | 57 |
| Helminthosporium sigmoideum var. irregulare IFO 5273 | 50 | S | 53 |
| Kloeckera africana IFO 0869 | 60 | S | 65 |
| Nectria cinnabarina IFO 6821 | 44 | S | 48 |
| Pseudomonas diminuta IFO 12697 | 41 | S | 50 |
| Phialocephala bacterospora IFO 8770 | 55 | S | 45 |
| Rhodotorula glutinis IFO 0395 | 42 | S | 53 |
| Saccharomyces cerevisiae AHU 3402 | 38 | S | 55 |
| Sterigmatomyces elviae DSM 70852 | 53 | S | 60 |
| Schizoblastosporion kobayasii IFO 1644 | 71 | S | 95 |

We claim:

1. A process for producing optically active 1,3-butanediol comprising contacting 4-hydroxy-2-butanone with viable cells of a microorganism or cells thereof which have been ground, acetone-treated, or lyophilized, selected from the group consisting of Agrobacterium radiobacter, Azotobacter chroococcum, Bordetella bronchiseptica, Brettanomyces abstines, Dekkera bruxellensis, Endomyces decipiens, Eremascus fertilis, Erwinia carotovora subsp carotovora, Fusarium oxysporum, Fusarium solani, Geotrichum fragrans, Gibberella fujikuroi, Gonatobotryum apiculatum, Klebsiella pneumoniae, Micrococcus luteus, Micrococcus roseus, Mycobacterium smegmatis, Neosartorya fischeri var spinosa, Oospora astringenes, Pachysolen tannophilus, Paecilomyces variotii, Paracoccus denitrificans, Preussia terricola, Saccharomycopsis fibuligera, Serratia marcescens, Syringospora claussenii, Septoria glycines, Sporopachydermia lactativora, Talaromyces flavus var flavus, Westerdykella multispora, Zygoascus hellenicus, and Zygozyma oligophaga capable of asymmetrically reducing 4-hydroxy-2-butanone into (R) -1,3-butanediol, and then recovering the (R)-1,3-butanediol thus formed.

2. The process of claim 1, wherein said microorganism is a member selected from the group consisting of Agrobacterium radiobacter IFO 12664, Azotobacter chroococcum IFO 12994, Bordetella bronchiseptica IFO 13691, Brettanomyces abstines DSM 70726, Dekkera bruxellensis IFO 1590, Endomyces decipiens IFO 0102, Eremascus fertilis IFO 0691, Erwinia carotovora subsp carotovora IFO 3830, Fusarium oxysporum IFO 7152, Fusarium solani IFO 5232, Geotrichum fragrans JCM 1749, Gibberella fujikuroi IFO 5268, Gonatobotryum apiculatum IFO 9098, Klebsiella pneumoniae IFO 12059, Micrococcus luteus IFO 3333, Micrococcus roseus IFO 3764, Mycobacterium smegmatis IFO 3153, Neosartorya fischeri var spinosa IFO 5955,

*Oospora astringenes* IFO 7001, *Pachysolen tannophilus* IFO 1007, *Paecilomyces variotii* IFO 4855, *Paracoccus denitrificans* IFO 12442, *Preussia terricola* IFO 7893, *Saccharomycopsis fibuligera* IFO 0103, *Serratia marcescens* IAM 1105, *Syringospora claussenii* IFO 0759, *Septoria glycines* IFO 5294, *Sporopachydermia lactativora* IFO 1867, *Talaromyces flavus* var *flavus* IFO 7231, *Westerdykella multispora* IFO 5813, *Zygoascus hellenicus* IFO 1575, and *Zygozyma oligophaga* IFO 10360.

3. A process for producing optically active 1,3-butanediol, comprising contacting 4-hydroxy-2-butanone with viable a microorganism or cells thereof which have been ground, acetone-treated, or lyophilized, selected from the group consisting of *Aciculoconidium aculeatum, Brettanomyces anomala, Clavispora lusitaniae, Cochliobolus miyabeanus, Corynespora cassiicola, Dactylium dentroides, Echinopodospora jamaicensis, Enterobacter cloacae, Hamigera avellanea, Helminthosporium sigmoideum vat irregulare, Kloeckera africana, Nectria cinnabarina, Pseudomonas diminuta, Phialocephala bacterospora, Rhodotorula glutinis, Saccharomyces cerevisiae, Sterigmatomyces elviae,* and *Schizoblastosporion kobayasii* capable of asymmetrically reducing 4-hydroxy-2-butanone into (S) -1,3-butanediol, and then recovering the (S)-1,3-butanediol thus formed.

4. The process of claim 3, wherein said microorganism is a member selected from the group consisting of *Aciculoconidium aculeatum* IFO 10124, *Brettanomyces anomala* IFO 0796, *Clavispora lusitaniae* IFO 1019, *Cochliobolus miyabeanus* IFO 6631, *Corynespora cassiicola* IFO 6724, *Dactylium dentroides* ATCC 46032, *Echinopodospora jamaicensis* IFO 9819, *Enterobacter cloacae* ATCC 7256, *Hamigera avellanea* IFO 7721, *Helminthosporium sigmoideum* var *irregulare* IFO 5273, *Kloeckera africana* IFO 0869, *Nectria cinnabarina* IFO 6821, *Pseudomonas diminuta* IFO 12697, *Phialocephala bacterospora* IFO 8770, *Rhodotorula glutinis* IFO 0395, *Saccharomyces cerevisiae* AHU 3402, *Sterigmatomyces elviae* DSM 70852, and *Schizoblastosporion kobayasii* IFO 1644.

5. The process of claim 1 or 3, wherein said contacting said 4-hydroxy-2-butanone comprises adding said 4-hydroxy-2-butanone to a culture medium in which said microorganism is grown, or to a buffer or water in which said microorganism is resuspended after separation of said microorganism from said culture medium.

6. The process of claim 5, wherein said contacting further comprises adding a carbon source.

7. The process of claim 6, wherein said carbon source is glucose or sucrose.

8. The process of claim 1 or 3, wherein said 4-hydroxy-2-butanone is added as such, dissolved in water, dissolved in an inert organic solvent, or dispersed in a surfactant.

9. The process of claim 1 or 3, wherein said 4-hydroxy-2-butanone is added either at once at the initiation of said process, or in portions.

10. The process of claim 1 or 3, wherein said contacting is carried out at a pH of from 3 to 9, at a temperature of from 10 to 60° C., for 1 to 120 hours, either under stirring or standing.

11. The process of claim 10, wherein said contacting is carried out at a pH of from 5 to 8 at a temperature of from 20° to 40° C.

12. The process of claim 1 or 3, wherein said 4-hydroxy-2-butanone is present at a concentration in the range from 0.1 to 10%.

13. The process of claim 1 or 3, wherein said microorganism or said cells thereof which have been ground, acetone-treated, or lyophilized are immobilized.

\* \* \* \* \*